United States Patent
Henkes et al.

(10) Patent No.: US 10,828,040 B2
(45) Date of Patent: Nov. 10, 2020

(54) VASCULAR IMPLANT

(71) Applicant: PHENOX GMBH, Bochum (DE)

(72) Inventors: Hans Henkes, Stuttgart (DE);
Hermann Monstadt, Bochum (DE);
Ralf Hannes, Dortmund (DE)

(73) Assignee: Phenox GmbH, Bochum (DE)

( * ) Notice: Subject to any disclaimer, the term of this patent is extended or adjusted under 35 U.S.C. 154(b) by 110 days.

(21) Appl. No.: 16/060,255

(22) PCT Filed: Dec. 14, 2016

(86) PCT No.: PCT/EP2016/080917
§ 371 (c)(1),
(2) Date: Jun. 7, 2018

(87) PCT Pub. No.: WO2017/102804
PCT Pub. Date: Jun. 22, 2017

(65) Prior Publication Data
US 2018/0360462 A1 Dec. 20, 2018

(30) Foreign Application Priority Data
Dec. 14, 2015 (DE) .................. 10 2015 121 757

(51) Int. Cl.
*A61B 17/12* (2006.01)
*A61F 2/90* (2013.01)
(Continued)

(52) U.S. Cl.
CPC .. *A61B 17/12172* (2013.01); *A61B 17/12118* (2013.01); *A61B 17/12177* (2013.01);
(Continued)

(58) Field of Classification Search
CPC ........ A61B 17/12113; A61B 17/12168; A61B 17/12172; A61B 17/12177
See application file for complete search history.

(56) References Cited

U.S. PATENT DOCUMENTS 4,425,908 A * 1/1984 Simon ................ A61F 2/01
128/899
8,323,309 B2 * 12/2012 Khairkhahan ..... A61B 17/0057
606/200

(Continued)

FOREIGN PATENT DOCUMENTS

DE 102008028308 4/2009
WO WO2012078678 6/2012
(Continued)

OTHER PUBLICATIONS

International Search Report from International Application No. PCT/EP2016/080917 dated Mar. 31, 2017.

*Primary Examiner* — Todd J Scherbel
(74) *Attorney, Agent, or Firm* — Crockett & Crockett, PC; K. David Crockett, Esq

(57) ABSTRACT

An implant (1) to be used for the occlusion of bifurcation aneurysms, with the implant (1) having an expanded state in which it is implanted in the blood vessel (Z) and a contracted state in which it is movable through the blood vessel (Z) and a proximal fixing section (3) a distal section (5) where the implant (1) is radially widened relative to the fixing section (3) and which is intended for placement in or in front of the aneurysm (A), and a transition section (4) located between the fixing section (3) and the distal section (5), wherein the implant (1). The implant is composed of interconnected or intersecting filaments (10) originating from the fixing section (3) or distal section (5) which meet centrally in the transition section (4), wherein the filaments (10) in the transition section (4) at least to some extent pass through a sleeve (7).

14 Claims, 11 Drawing Sheets

(51) Int. Cl.
  *A61F 2/82* (2013.01)
  *A61B 90/00* (2016.01)
  *A61F 2/07* (2013.01)
  *A61F 2/06* (2013.01)

(52) U.S. Cl.
  CPC ...... *A61F 2/90* (2013.01); *A61B 2017/12063* (2013.01); *A61B 2017/12068* (2013.01); *A61B 2090/3966* (2016.02); *A61F 2/07* (2013.01); *A61F 2002/065* (2013.01); *A61F 2002/823* (2013.01); *A61F 2220/0075* (2013.01); *A61F 2230/005* (2013.01); *A61F 2230/0093* (2013.01); *A61F 2250/0039* (2013.01); *A61F 2250/0048* (2013.01); *A61F 2250/0098* (2013.01)

(56) References Cited

U.S. PATENT DOCUMENTS

| | | |
|---|---|---|
| 2006/0064151 A1 | 3/2006 | Guterman et al. |
| 2007/0270902 A1 | 11/2007 | Slazas et al. |
| 2009/0012559 A1 | 1/2009 | Chanduszko |
| 2011/0046719 A1 | 2/2011 | Frid |
| 2012/0245675 A1* | 9/2012 | Molaei ............. A61B 17/12118 623/1.16 |
| 2014/0058420 A1 | 2/2014 | Hannes et al. |
| 2015/0250628 A1 | 9/2015 | Monstadt et al. |

FOREIGN PATENT DOCUMENTS

| | | |
|---|---|---|
| WO | WO2012113554 | 8/2012 |
| WO | WO2014029635 | 2/2014 |

* cited by examiner

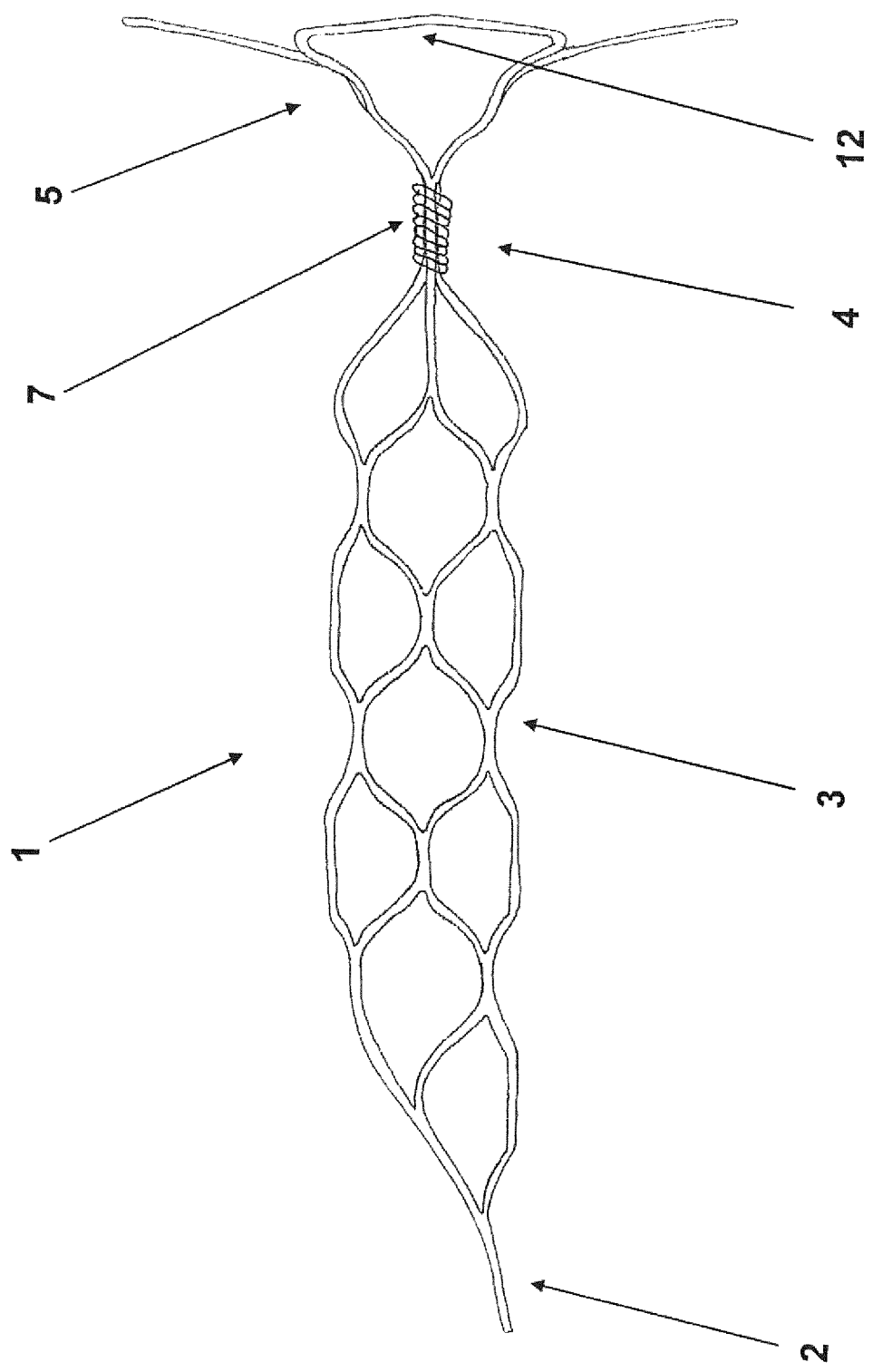

VASCULAR IMPLANT

FIELD OF THE INVENTIONS

The invention relates to an implant to be used for the occlusion of aneurysms in blood vessels in the region of vascular branches, in particular bifurcation aneurysms, with the implant being in an expanded state in which it is implanted in the blood vessel and in a contracted state in which it is movable through the blood vessel, with the implant having a proximal fixing section by means of which the implant can be secured to the wall of a blood vessel, a distal section where the implant is radially widened relative to the fixing section and which is intended for placement in or in front of the aneurysm, and having a transition section located between the fixing section and the distal section, wherein the implant is composed of interconnected or intersecting filaments and one or more filaments originating from the fixing section or distal section meet centrally in the transition section. Using a catheter and guidewire such an implant is to be transported to the placement site for the purpose of implanting it permanently. Accordingly, the invention also relates to such an implant which is attached to a guidewire so as to be ready for implantation. Furthermore, the invention relates to a method for placing the implant in position.

BACKGROUND

Arteriovenous malformation may significantly impair a patient and may even result in fatal risks. This applies, in particular, to aneurysms, especially when these are found to exist in the cerebral region. Usually it is attempted to occlude malformations of this nature by means of implants. In most cases, such implants are placed by endovascular methods using catheters.

Especially in the treatment of cerebral aneurysms, implanting platinum spirals has proven its worth, said spirals fill the aneurysm more or less completely, largely obstruct the blood inflow and enable a local thrombus or clot to form which fills and ultimately closes off the aneurysm. Nevertheless, this treatment approach is only suited for the treatment of aneurysms that have a relatively narrow access to the vessel system, so-called aciniform aneurysms. In the event of blood vessel protuberances having a wide access to the blood vessel, there is a risk that the implanted spirals or coils may be flushed out again and cause damage to other areas of the vascular system. In such cases it has already been proposed to place into position a kind of stent that "bars" the opening of the aneurysm and in this way prevents the occlusion coils from being flushed out. Such stents are designed to have a relatively wide-mesh wall and are being employed in the treatment of some forms of aneurysms.

Vessel branches, in particular vessel bifurcations are a quite frequently occurring phenomenon. In the event of a weak vessel wall, the blood stream flowing through an artery and acting on the front wall in a bifurcation quickly causes a protuberance or bulge which is prone to rapidly dilate further. More often than not, such bifurcation aneurysms have a wide neck which prevents a therapy to be performed with occlusion coils only.

Vascular implants that are suitable to bring about such a "barring" of the aneurysm entrance in the area of a vascular branching have, for example, been disclosed in the international patent applications WO 2012/113554 A1 or WO 2014/029835 A1. The aneurysm can then be rendered non-hazardous as a result of occlusion coils inserted after the implant has been placed in position. It is also possible that the implant itself separates the aneurysm sufficiently from the blood flow. For this purpose, for example, the implant may have a membrane that is placed in the area of the aneurysm neck or in front of the aneurysm neck. If considered useful or expedient, the blood inflow to the aneurysm can also be reduced with filaments, typically wires of small diameters, to such an extent that the additional introduction of occlusion coils or other occlusion means into the aneurysm can be dispensed with.

Implants known from the state of the art have a proximal section that is used to secure the implant in the vascular vessel and is essentially provided in the form of a conventional stent. A distal portion or section is provided at the distal end of the implant to be placed in or in front of the aneurysm which serves to cut off the aneurysm from blood flow and/or prevent occlusion means introduced into the aneurysm from exiting the aneurysm and entering the blood vessel. An intermediate section may be provided between the proximal and distal sections that for example has a relatively low density of filaments to avoid or minimize the obstruction of the blood flow into the branching blood vessels.

The problem with the placement of implants suitable for bifurcation aneurysms has turned out to be that many aneurysms have an irregular shape, for example they are not symmetrical or tilt to one side. In this respect, a high flexibility of the distal section of the implant intended to lie in or in front of the aneurysm, is advantageous. Accordingly, in WO 2012/078678 A1, for example, it is proposed to provide a very narrow intermediate section consisting of one or more filaments.

However, this has also proved insufficient for some aneurysms, as the wires situated in the intermediate section are either too torsionally rigid to allow good adaptation to the aneurysm or tend to spread laterally, which in turn hinders the flow of blood into adjacent blood vessels or may even result in blood vessels to become damaged.

It is, therefore, the objective of the present invention to provide an implant for the occlusion of aneurysms in blood vessels in the region of vascular branches, in which the distal section can adapt in a particularly flexible manner to the shape of the respective aneurysm.

SUMMARY

This objective is achieved by an implant to be used for the occlusion of aneurysms in blood vessels in the region of vascular branches, in particular bifurcation aneurysms, with the implant being in an expanded state in which it is implanted in the blood vessel and in a contracted state in which it is movable through the blood vessel, with the implant having a proximal fixing section by means of which the implant can be secured to the wall of a blood vessel, a distal section where the implant is radially widened relative to the fixing section and which is intended for placement in or in front of the aneurysm, and having a transition section located between the fixing section and the distal section, wherein the implant is composed of interconnected or intersecting filaments and one or more filaments originating from the fixing section or distal section meet centrally in the transition section, wherein the filaments in the transition section at least to some extent pass through a sleeve.

As proposed by the invention, originating from the fixing section the implant, when viewed in the longitudinal direction, converges narrowly in the transition section and then widens again in the distal section. The cross section of the implant in the longitudinal direction is thus considerably smaller in the transition section than in the distal section or in the fixing section. In the transition section, only one or more filaments are located close to each other. These filaments run at least to some extent through a sleeve that holds the filaments together in the transition section. In this context, it is to be understood by "to some extent" that the filaments in the transition section do not necessarily have to extend through the sleeve over their entire length; it is sufficient if part of the length of the filaments in the transition section is embraced by the sleeve. In other words, the sleeve can be shorter than the transition section and the filaments that form the transition section.

The filaments of the transition section may be separate filaments that on the one hand are attached to the distal section and, on the other, to the fixing section. However, it is preferred that these filaments are the same filaments that also form the fixing section and the distal section and only converge centrally in the area of the transition section.

Because the filaments are held together in the transition section by a sleeve surrounding the filaments, the filaments remain movable relative to each other to a certain extent, but nevertheless are prevented from expanding radially beyond the intended extent. This eliminates the risk of one or several filaments spreading radially in the transition section. Nevertheless, the implant is very flexible around the transitional section and for that reason is capable of adapting well to the shape of the blood vessels and the aneurysm. Other conceivable methods of fixing the filaments together might also make it possible to minimize the risk of the filaments to spread radially but would result in the mobility of the filaments to be severely restricted and thus would substantially impair the flexibility of the implant. The invention is particularly important for the treatment of strongly asymmetric aneurysms and aneurysms that tilt to one side.

Due to the particularly thin design of the transition section it is also ensured that the flow of blood to branching off vessels is not or hardly impaired. In other words, the fixation section results in securing the implant in the carrier vessel, the transition section provides for sufficient flexibility as well as an unimpeded blood flow to and from vessels that branch off, and the distal section provides for the occlusion of the aneurysm, whereby the distal section can either directly minimize the flow of blood into the aneurysm or ensure that the occlusion means introduced into the aneurysm remain in the aneurysm.

Depending on the shape of the aneurysm and the shape of the implant, the distal section can be placed in the aneurysm itself or in front of the aneurysm, i.e. in front of the aneurysm neck on the side of the carrier vessel. In this context, a placement in the aneurysm is also considered to be a placement in the neck of the aneurysm, said neck forming part of the aneurysm. As a rule, the distal section is positioned in the entry area of the aneurysm.

Within the meaning of the invention, the term "sleeve" is to be understood broadly, that is, it may be provided in the form of a short tube, but also other shapes or configurations may be used, provided that the sleeve has an inner cavity through which the filaments can pass. For example, the sleeve can be provided in the form of a collar. In particular, the sleeve can also be a wire coil that has an inner cavity.

It is important that the sleeve does not slip or be displaced when the implant is contracted and possibly moves into the area of the fixing section or the distal section. In this case it could happen that the sleeve hinders the expansion of the implant after it has been liberated. Provided that a corresponding slipping of the sleeve is not excluded by the dimensions of the individual sections of the implant anyway, it may therefore make sense to arrange for stoppers proximal and/or distal to the sleeve, said stoppers shall prevent the sleeve from slipping or being displaced beyond the location of the stoppers. Said stoppers may be provided, for example, in the form of radial extensions in the transition section.

Another way to prevent the sleeve from slipping is to provide one or several filaments in the transition section with an eyelet, with the sleeve extending through the eyelet in any case sectionally, so that the sleeve is restricted in its mobility in the longitudinal direction of the implant. The eyelet can be created, for example, by one or several of the filaments having a larger cross-section in the transition section and by an opening existing in the filament in the area of the larger cross-section. Typically, the opening has an oblong form, so that a certain amount of longitudinal movement of the sleeve is allowed to ensure sufficient flexibility, but the longitudinal movement is limited by the distal and proximal ends of the eyelet. Normally, the opening is substantially orthogonal to the longitudinal axis of the implant. As a rule, the eyelet in the respective filament is located on the outer side so that the filament is otherwise surrounded by the sleeve, and with the sleeve extending through the eyelet. However, the reverse case is also conceivable, in which the eyelet points from the respective filament towards the center of the transition section; in this case as well, the sleeve extends through the eyelet, but the rest of the filament is situated outside the sleeve.

It is particularly advantageous if the sleeve is at least partially made of a radiopaque material. This, typically together with other radiopaque markers on the implant, enables visualization to be performed and thus control of the implantation process. Of preference in this context are platinum, platinum alloys such as platinum-iridium or gold. It is possible to produce the sleeve, for example the wire spiral or coil, from the relevant material, but a coating, for instance, a gold coating is also conceivable.

In order to maintain a certain mobility of the filaments towards each other, it is preferred that the filaments run parallel to each other in the transition section. A slight twisting of the filaments is also conceivable, but this should not be too stiff in order not to endanger the adaptability of the implant.

As regards the placing process of the implant, the terms "proximal" and "distal" are to be understood such that they refer to parts of the implant that point towards the attending physician (proximal), or, as the case may be, to parts that point away from the attending physician (distal). Typically, the implant is thus moved forward in distal direction with the aid of a catheter. The term "axial" refers to the longitudinal axis of the implant extending from proximal to distal while the term "radial" denotes levels/planes extending vertically thereto.

The implant according to the invention may be provided with a mesh structure which may consist of a braiding of individual wires, with a mesh structure cut from a tube or with a mesh structure being a combination of the two. In that regard, the implant in general is to be viewed as a stent or stent-like object distinguished by its specialized way of application and design. In particular, the similarity to a stent applies to the fixing section, while the distal section is widened radially outwards and may, for example, be provided with outwardly facing arches. In the event of a braiding comprising single filaments, a number of 3 to 24 filaments is preferred for the fixing section.

The filaments that are used to form the implant are in most cases wires or webs, in particular made of metal. Particularly preferred is the use of shape memory metals such as nickel-titanium alloys, also known under the name nitinol. Ternary nickel-titanium alloys can also be put to use. It is also possible to make use of other conventional stent materials such as medical steel or cobalt-chrome alloys.

The filaments can have a round, oval, square or rectangular cross-section. Flat filaments in the form of thin strips, especially metal strips can be employed as well.

One or several coupling elements can be arranged at the proximal end of the fixing section. In particular, the fixing section can merge proximally into the coupling elements. Said coupling elements are preferably situated at the periphery, that is, eccentrically arranged over the circumference of the implant in its expanded form, and when placement is done are in contact with the vessel wall when the implant has assumed its expanded form. The coupling elements serve to connect the implant with an insertion aid, especially a guidewire.

The eccentric arrangement of the coupling element(s) at the proximal end of the fixing section facilitates retraction of the implant into the placement catheter in the event of a misplacement. Preferred are embodiments comprising between one and three coupling elements. Preferably, the coupling elements consist of coupling wires. The provision of several coupling elements leads to an improvement of retractability, especially when the fixing section is relatively short. The detachable connection of the coupling elements with the insertion aid can be designed in different ways, preferably as an electrolytically detachable connection as it is known from the state of the art. Also conceivable are thermal or mechanical detachment systems.

The coupling elements, especially the coupling wires, respectively the proximal end of the implant (without introducer sheath) may in the expanded state liberated from external constraints form an angle of between 0° and +60° in relation to the longitudinal axis of the implant, wherein a positive angle denotes a proximal end pointing outwards. Preferred is a range of between +10° and +30°, with the optimum angle depending on the configuration of the vessel. Such a positive angle facilitates an optimum expansion of the implant and enables the proximal end to be optimally located in the carrier vessel so that said proximal end is effectively prevented from projecting into the vessel lumen where it could interfere with the blood flow or insertion of another microcatheter. Preferably, the proximal end of the implant is of atraumatic design to make sure the vessel wall remains unharmed. According to the invention, the formation of the angle is to be understood in such a way that the angle does not have to exist in the contracted state, i.e. it is sufficient to impress a corresponding deformation on the implant in the expanded state. In particular the use of shape memory materials is considered conducive in this context.

With the fixing section, the implant rests on the wall of the blood vessel in which the implant is implanted and is secured in this way. In this area, the vessel is not damaged and capable of supporting the fixing section which is similar to a stent wall. In the event of self-expanding implants, the fixing section is automatically brought in contact with the vessel wall when the implant has been liberated from the catheter whereas implants placed in position and dilated by means of balloons are pressed against the vessel wall in this area via a placement balloon. Self-expanding implants are preferred.

In comparison to the fixing section and even more so to the transition section the distal section is radially enlarged outwardly. It is used for placement in the aneurysm itself or in the area of access to the aneurysm, that is, at the aneurysm neck which it closes off, or it prevents occlusion means introduced into the aneurysm from exiting. Of primary importance is that blood coagulation ultimately takes place in the aneurysm. On the one hand, the surface coverage must be sufficiently large to either prevent any occlusion means introduced into the aneurysm from exiting the aneurysm or, due to an adequate amount of material, create a dense surface; on the other hand, a sufficient degree of flexibility of the implant must still be maintained to enable it to be introduced in the area of the bifurcation aneurysm.

When in expanded state, the distal section may be provided with struts, loops or arches pointing radially outwards which serve to anchor the implant in or in front of the aneurysm. Therefore, the implant often shows a blossom shape in the distal section when viewed from the distal side. As a rule, there are at least two struts/loops/arches, in particular three struts/loops/arches or more. Typically, the number of struts/loops/arches ranges between 1 and 24, preferably between 2 and 8. Said struts, loops or arches may be made from appropriately formed wire elements but in the event the implant is cut from a tube they may also be produced by adopting a laser cutting method to which said tube is then subjected, normally followed by a heat treatment. Said struts, loops or arches can be attached by adopting a laser welding method, for example. In the event loops or arches are provided these preferably consist of wire elements originating from the transition section, then forming a bend and returning thereto, wherein said loops/arches may basically have an optionally complex configuration. These may in particular also be three-dimensional objects depending on the shaping or configuration of the loops or arches. The loops or arches should be largely atraumatic and ensure that the sensitive vessel wall of the aneurysm remains unharmed. However, other filaments or struts may also be employed by means of which a radial expansion/enlargement of the distal section is achieved in comparison to the fixing section and the transition section. Said expansion may, for example, be of trumpet-, basket-like or blossom shape or provided in the form of a braiding. Outwardly protruding struts are preferably concentrically aligned radially inwards. At the same time the struts may protrude in distal direction. For example, two or more struts can each originate from a mutual connection point.

The angle the struts/loops/arches form in relation to the longitudinal axis of the implant after placement ranges between −45° and +175°, wherein a positive angle is indicative of struts/loops/arches pointing radially outward and a negative angle of struts/loops/arches pointing radially inward. In the event of relatively regular bifurcation aneurysms the angle preferably is in the range of between +45° and +90°; on the other hand, aneurysms are occasionally encountered that have an irregular shape, in particular a highly asymmetric shape. In such cases it may prove expedient to provide for significantly deviating angles of the struts/loops/arches. It may be useful, for instance, to provide for a very large angle in cases where the wall in one area of the aneurysm is strongly bulging out towards the blood supplying vessel. In such cases, angles >90° are conceivable. In other cases, it may be helpful to provide for part of the struts/loops/arches to point inwards, that is, select negative angles to enable adaptation to the wall of the aneurysm. However, the flexibility that is achieved trough the very narrow transition section provided with a sleeve ensures that the struts/loops/arches are capable of adapting well to the shape of the aneurysm even without providing for particularly large or small angles being preset. The angles may vary; in the event of an asymmetric aneurysm it may, for example, be helpful and expedient to provide for some loops to have angles >90° whereas other loops form customary angles ranging between 45° and 90°. It is of importance that said angles are formed after placement has been completed; therefore, also an implant in which the angles indicated here have not yet formed when in a condition prior to implant placement, possibly due to external forces, is to be considered to fall within the scope of the invention.

Angles that the struts/loops/arches form in relation to the longitudinal axis of the implant may, for example, range between 45° and 90°, −45° and 0°, 90° and 135° or 135° and 175°.

The struts/loops/arches in the distal section may be continuations of the filaments forming the remaining implant structure but may as well be separate filaments attached in the distal region of the remaining implant structure, that is, at the distal end of the transition section, for instance by adopting a laser welding technique. In this context, each strut, each loop or each arch of the distal section may be connected to the remaining implant structure via one or a plurality of connection points, in particular only one or two connecting points per loop/strut/arch may be provided.

As an alternative to the design of the distal section comprising loops or arches, the distal section can also be spherical, mushroom-shaped, anchor-shaped or ellipsoid-shaped. A spherical section, for example, can well adjust itself to the inner wall of the aneurysm because a regular bifurcation aneurysm often exists basically in the form of a sphere. It is to be noted in this respect that within the scope of the invention a spherical form need not only be a true sphere as per its geometrical definition but may also be of deviating round, three-dimensional shape which are deemed to be spheres as proposed by the invention. In some cases, the form of section is also comparable to an ellipsoid but it shall also be understood here that this need not be an exact spheroid in order to be regarded as ellipsoidal within the meaning of the invention. Moreover, sections may also have mushroom- or anchor-like shapes which are in particular suitable for the treatment of irregular aneurysms, for example if a wall portion of an aneurysm shows significant bulging in the direction of the supplying vessel. In the event of a mushroom or anchor form this is achieved in that some areas of the section extend in proximal direction. It shall be understood here as well that a section of mushroom- or anchor-like shape may also be asymmetric, for example may have areas that only on one side extend in proximal direction. The distal section may be made by laser cutting techniques or of braided design, with between 8 and 128 filaments being preferably employed.

In the distal section, a central area may be provided with a view to obstructing the aneurysm, that is, to prevent the escape of occlusion means and/or to separate the distal section from the flow of blood. The elements provided for this purpose are referred to as separation elements. On the one hand, the area may be designed to comprise introduced fibers, threads, thin wires, a membrane or similar separation elements but, on the other hand, may also be an integral part of the implant in the sense that the separation elements may be cut out of the basic tube and appropriately transformed or be composed of a wire braiding, for example in the shape of loops or strings. In the event of loops or strings these elements point radially inwards into the lumen of the implant, other than the above described loops of the distal section that at least for the most part point outwards. To make sure the inwardly arranged loops/strings do not interfere with each other it may be expedient to have them designed asymmetrically. The number may vary depending on the structure of the implant.

The threads making up the separation elements may be made of a polymer material, for example a polyamide such as nylon (polyhexamethylene adipic acid amide). It is also possible to use metal for this purpose, with shape memory alloys being preferred, in particular nickel titanium alloys such as nitinol.

Another possibility is to provide a membrane as separation element, said membrane being largely or completely impermeable to blood and in this way capable of separating the aneurysm from the blood flow. In the event the aneurysm can almost completely be isolated from the blood flow an introduction of occlusion means into the aneurysm may, circumstances permitting, be dispensed with so that the separation element in this case does not serve to retain occlusion means. The membrane can be fixed to the filaments and/or stretched on a braid of threads or wires, e.g. threads or wires can form a structure over or onto which the membrane is stretched. Additionally, further threads/wires are conceivable which, for example, may extend or be arranged to form a cross or crosshairs. Nevertheless, an arrangement of threads or wires is not necessarily needed for this purpose, the central area of the distal section may also be spanned over without the use of additional threads or wires.

The provision of a membrane as separation element is to be considered advantageous in that said membrane compactly folds together in distal or proximal direction when the implant is placed in the catheter so that an implant can be made available that in expanded condition has a largely impermeable separation element and when in contracted state is capable of easily passing also through narrow blood vessels. Otherwise, in comparison to an implant without separation element the structure of the implant described hereinbefore is largely the same.

However, even in cases where a membrane is provided as separation element it may still be of advantage to additionally introduce occlusion means into the aneurysm. For this reason, it may be expedient to use a membrane that has one or several cutouts so that occlusion means, in particular coils, can be placed into the aneurysm through these cutouts. Said cutout should be appropriately sized such that a catheter can be pushed through it into the area of the aneurysm, with the placement of the respective occlusion means being done via this catheter. On the other hand, the neck of the aneurysm should be covered to such an extent that the occlusion means are prevented from exiting the aneurysm in an uncontrolled manner, with any threads/wires spanning the area of the membrane in this case may perform an additional retaining function. It goes without saying in such a case that the threads or wires must not be spaced too closely so as not to interfere with a catheter passing through and introducing the occlusion means.

To enable occlusion means to be introduced into the aneurysm, the membrane may also be designed so as to be pierceable partially, with such a piercing effect being typically brought about by a microcatheter or guidewire. Through the opening so created a microcatheter is then run, through which the occlusion means are placed in position. The membrane should be designed in such a such way that after it has been pierced it remains partially intact to ensure it continues to prevent the occlusion means from exiting again. For example, threads or wires arranged as additional separation elements that may be arranged in the form of crosshairs can ensure that only a segment of the membrane forms an opening when being pierced whereas the other segments of the membrane remain covered due to the fact that the marginal areas of the membrane are stabilized and safeguarded by the threads/wires against rupturing. The membrane being provided as separation element may either be a single membrane which is to be pierced only partially or may consist of several smaller membranes.

Instead of or in addition to providing a membrane as separation element, it may be useful or expedient to arrange membranes in the interior of the (wire)loops or arches forming the distal section. Membranes may also be provided between struts of the distal section. Also, spherical, mushroom-, anchor- or ellipsoid-shaped distal sections can be covered with a membrane. When placed in front of or in the entry area of the aneurysm, the membranes can either be used to deflect the blood flow into branching vessels or to prevent the flow of blood into the aneurysm.

The membrane need not be limited to the separation element and the interior of the loops/arches but may span the totality of distal section, so that the struts, loops or arches may serve to hold the membrane in place. For example, membranes may be arranged in the interspaces between the struts, loops or arches.

Even if the distal section is formed, wholly or in part, by filaments other than loops it is possible to arrange membranes in this location. For example, one or several membranes may be put up by means of struts protruding radially outwards. In such a case the structure resembles an umbrella, that is, when the distal section is expanding the unfolding struts put up between them form one continuous or several membranes. By providing a plurality of struts and in this way a corresponding number of strut ends a larger and more circular area can be covered by the membrane resulting in the interspaces to be reduced in size.

For the purpose of delimiting and reinforcing the membrane, threads may also be spanned between the individual struts/loops/arches, that is, the membranes are limited at least partially at the sides by one or several threads serving to connect the struts/loops/arches with each other. Such a delimiting of the relevant membrane must not necessarily take place via a thread in every direction, even the struts/loops/arches themselves may to some extent serve this purpose. For example, the outer edge of the membrane which is often situated further distally may be bordered by threads while the inner edge be formed by struts/loops/arches. In comparison to a membrane without delimitation at the sides an additional protection of the membrane is achieved in this way so that damage and cracks can be avoided. The threads are preferably made of a polyamide such as nylon.

The membrane (whether used as a separation element or located in other areas of the distal section) may be made of a polymeric material such as polytetrafluoroethylene, polyester, polyamides, polyurethanes or polyolefins. Especially preferred are polycarbonate urethanes. It is especially desirable to provide for an integral connection of the membrane with the threads or wires provided, where applicable, as additional separation elements. Such a connection may be achieved by coating the threads/wires by immersion or spraying techniques.

Preferably, the membrane is produced by an electrospinning process. By applying an electric current, fibrils or fibers are separated from a polymer solution and deposited on a substrate. Said deposition causes the fibrils to agglutinate into a non-woven fabric. As a rule, the fibrils have a diameter ranging between 100 and 3000 nm. Membranes created by electrospinning have a very uniform texture and may embrace or include in them a basic structure comprising threads or wires. The membrane is tenacious, withstands mechanical stresses, and can be pierced mechanically without an opening so created giving rise to cracks propagating from it. The thickness of the fibrils as well as the degree of porosity can be controlled by selecting process parameters as appropriate. In the context of producing the membrane and with respect to materials suitable for this purpose, special attention is drawn to publications WO 2008/049386 A1, DE 28 06 030 A1 and literature referred to therein.

Also of advantage is an implant that uses as separation element a membrane which is in contact with the inner side of the implant, wherein said membrane in turn is permanently attached to further outer membrane sections filling out the individual loops or arches of the distal section. Such a membrane structure can be produced by electrospinning. In this case, the inner and outer membrane sections are partially connected; where the inner membrane section has no connection with the outer membrane section, it contracts similar to a nylon stocking, resulting in an opening for the introduction of occlusion means being created.

Instead of adopting an electrospinning method, the membrane may also be produced by an immersion process.

The membrane serving as separation element must not necessarily be arranged orthogonally to the longitudinal axis of the implant but may also be oriented towards proximal. Although the membrane in its peripheral area is secured in this case to the circumference of the implant, the middle region of the membrane, however, extends in proximal direction. In this way, a conical or pyramid shape is formed wherein the base of the cone/pyramid is oriented orthogonally to the longitudinal axis, with the membrane in its peripheral region being attached to the implant whereas the apex of the cone/pyramid is situated further to proximal. In this manner, the flow of blood is divided and directed sideways when coming into contact with the membrane so that the ingress of blood into the aneurysm is largely prevented.

Even if the membrane provided as separation element has a conical or pyramid shape, said membrane may also be provided with one or a plurality of cutouts to make sure occlusion means may continue to be introduced into the aneurysm through said cutouts after the implant has been placed in position.

To make sure the conical or pyramid shape of the membrane can be maintained on a permanent basis, the membrane should be secured to a framework structure of threads or wires, but basically this structure may also consist of strings/lands cut, for instance by means of a laser, out of the structure forming the implant. Care must be taken in this case that the threads/wires are of adequate stiffness to prevent the membrane from undergoing reorientation or turning inwards as a result of the blood pressure. It may be necessary in this respect to introduce additional threads or wires.

Another possibility is to create crosshairs consisting of two relatively long individual threads to which the membrane is attached, with the membrane initially not being tensioned due to the length of the individual threads. Moreover, one or several threads may be attached to a further proximally situated loop of the implant so that the crosshairs and thus the membrane is spanned/tensioned in proximal direction as soon as the implant undergoes stretching. It shall be understood, however, that the crosshairs must not necessarily be composed of two threads only but other thread braidings of nearly unlimited configuration are conceivable as well that establish a type of framework impressing a structure onto the membrane.

Generally speaking, it is of importance for the invention that the distal section, possibly with the separation element, performs its intended function which is to reliably retain occlusion means, for example occlusion coils, introduced into the aneurysm or deflect the flow of blood in such a manner that further occlusion means are not needed. The separation element also has at least one component arranged orthogonal to the longitudinal axis of the implant.

If the separation elements are formed by the insertion of fibers, threads or thin wires, it is advisable to arrange eyelets in the distal section to which the threads are secured by knotting using a cross- or star-shaped pattern. The eyelets proper may be made of fiber material. The threads/fibers consist, for example, of a suitable polymer such as a polyamide (nylon) or be composed of metallic fibers.

However, arches or (wire) loops cut from a tube material and bent into the implant body may also be used as separation elements. At least one arch/one loop is required for this purpose. If between two and four arches/loops are used, these will form a stable separation element which reliably retains the occlusion means introduced into an aneurysm.

When contracting the implant, the loops are typically stretching in proximal direction and thus lean against the other filaments of the implant so that the implant may be easily moved through a catheter without causing problems. Slot-shaped openings can be left between the loops through which occlusion means can be inserted into the aneurysm. Alternatively, it is also possible, however, to provide the loops and/or the interspaces between the loops with a membrane to enable an impermeable as possible separation element to be achieved. Basically, membranes may also be used that are provided with one or several openings.

With regard to the various possibilities of designing the separation elements or providing the distal section with membranes, reference is also made to WO 2014/029835 A1, the content of which is also to be the subject of the disclosure of the present invention.

Walls of aneurysms are rather delicate and may rupture when forces are applied so this must by all means be prevented. To this end, especially the distal section of the inventive implant should be designed so as to be atraumatic. This is achieved, for example, by an arrangement of loops or arches that adjust gently to the wall of the aneurysm in places where they are in contact. Same as other regions of the implant, such loops or arches may be produced by laser cutting from a tube, created by means of affixed wires or produced by a uniform wire braiding.

In the distal section, all wire ends should be made so as to be atraumatic to prevent perforation of the aneurysm wall.

The implants proposed by the invention may be provided in the fixing section in the form of a continuous laterally closed tube having a mesh structure but may also be slotted at the side either partially or all the way through. This slotted configuration may extend axially parallel or be of oblique/helical arrangement. In such a case, the mesh structure in the slotted areas is coiled up to suit the shape of the vessel, for example in the form of a rolled segment of a wire mesh fence. During placement, such a slotted implant is capable of suitably adapting to the vessel lumen, especially of the supplying vessel, with a slight underlap (gap) or overlap of the lateral edges of the mesh structure being as a rule viewed to be unproblematic. Surprisingly, the slotted configuration does not have to exert a negative influence on the radial force, but on the other hand, such an implant generates less resistance when pushed through the catheter.

It is possible to provide at least some of the meshes of the implant in the fixing section with breaks, that is, some of the meshes are not completely closed. Such an open-cell design affords higher flexibility which may offer benefits when treating highly tortuous blood vessels. Moreover, the omission of strings/struts will enhance the flow of blood in the area of the vessel branching. However, such an advantageously increased flexibility has a drawback in that it will be more difficult or even impossible to retract an implant of open-cell design into the microcatheter in the event this becomes necessary during placement. For that reason, the proximal attachment to an introducer sheath may be omitted with such an embodiment. An alternative introducer system may, for example, be designed such that the implant radially compressed within the microcatheter rests on a wire between two cams and automatically unfolds when the microcatheter is removed and in this manner disconnects from the introducer system.

As a rule, the implants according to the invention are provided with radiopaque marker elements facilitating visualization and their positioning at the placement site. In particular, the sleeve provided in the transition section may be such a marker element. Moreover, marker element can be arranged, for example, in the area of the distal end of the distal section and may shape the connection points of joined wires so as to be atraumatic. Such marker elements can also be provided in the form of wire windings, as collars and slotted tube sections that are secured to the implant. For example, marker coils surrounding the filaments that are forming the loops can be provided as marker elements, whereby as a rule not the entire loops but, for example, only half of them are surrounded by marker coils. For said marker elements, in particular platinum and platinum alloy materials are suitable, for example alloys of platinum and iridium, as they are frequently used according to the state of the art for marking purposes and as material for occlusion coils. Ideally, the distal section and in particular the loops/struts/arches in the distal section are completely or in part provided so as to be radiopaque, i.e. they are made to be visible during radiography.

It is also possible to make use of radiopaque substances in the membranes. These may be radiopaque particles as they are customarily employed as contrast medium for x-ray technological purposes. Such radiopaque substances are, for example, heavy metal salts such as barium sulfate or iodine compounds. A radiopaque membrane proves beneficial during placement of the implant and for localization purposes and may be used either additionally to or instead of marker elements. Another alternative is a partial gold coating of areas of the implant, such as the loops or certain areas of the loops.

If thought expedient, part of the implant may be formed using struts of thinner cross section to increase the implant's flexibility. Preferably, the area is situated in the fixing section and intended to meet requirements associated with an irregular blood vessel configuration in the fixation zone.

The implants must not necessarily be of tubular structure but may also be provided in the form of rolled up "mats" that are braced in position against the wall of the vessel. The implants may also be partially slotted.

Furthermore, the invention relates to an implant in accordance with the description hereinbefore, said implant being coupled to a guidewire. Such an attachment may, for example, be brought about by means of connection elements dissolving electrolytically under the influence of electric current. Such connection elements and materials have often been described in particular for the severance of occlusion coils and stents. To accelerate electrolytic severance and concentrate the current on the connection element, it makes sense for the connector to be electrically insulated from the actual implant. Alternatively, although the implant itself can in fact be conductively connected to the connection element, it can otherwise be electrically insulated in its entirety, in particular by an electrically insulating coating. This can be achieved by a plastic coating, for example by using Parylene C.

Also, a mechanical detachment through coupling elements may be realized without difficulty, with such coupling elements appropriately interacting with suitably designed coupling parts of the guidewire. Under the external restraint of a catheter or enclosure this connection remains intact; however, after the implant and its coupling location have been released from the catheter or enclosure the attachment disconnects causing the implant together with the coupling elements forming part of the implant to be liberated.

Another variant is the thermal detachability of the implant.

The invention also relates to a procedure for introducing the implant according to the invention into the blood vessel system. This can be brought about with the help of a customary microcatheter, which is a proven and frequently adopted technique. In case the neck of the aneurysm is not sufficiently sealed off already by the separation elements alone, occlusion means are introduced into the aneurysm after the implant has been placed in position. For this purpose, the distal end of a microcatheter is moved into the aneurysm following which the occlusion means, in particular coils, are released. When this has been done the microcatheter is retracted while the implant prevents the occlusion means from escaping from the aneurysm. Aside from customary occlusion means such as coils bodies of other shape and configuration may also be employed to the close off aneurysms, for example spherical bodies of a braided design or formed differently.

BRIEF DESCRIPTION OF THE DRAWINGS

Further elucidation of the invention is provided by way of example through the enclosed figures where

FIG. 2*a* illustrates an inventive implant seen from the side;

DETAILED DESCRIPTION

Figure 1:
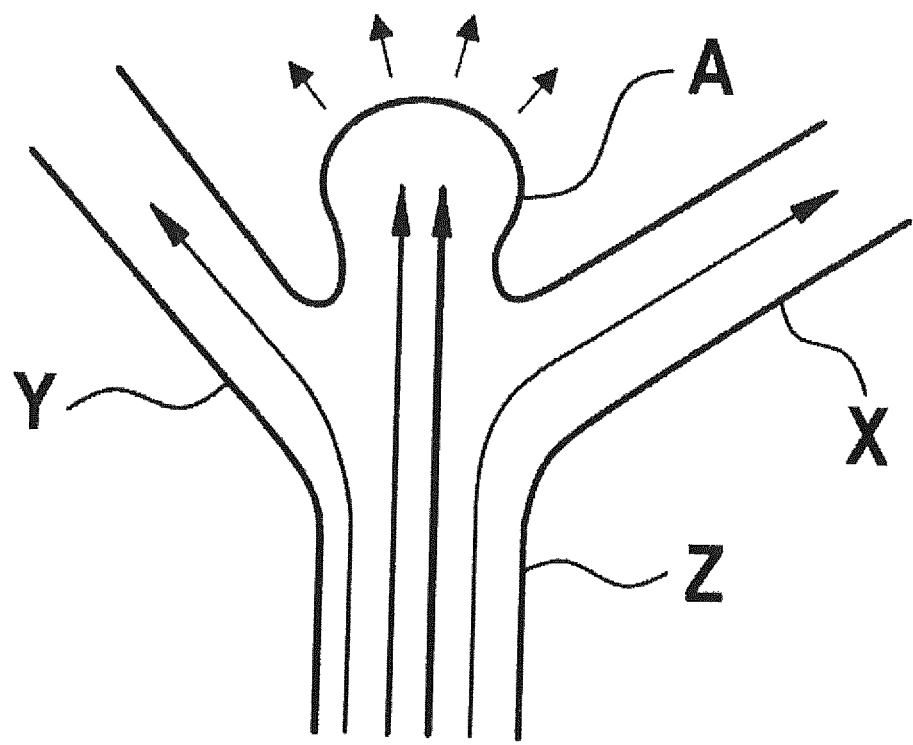
FIG. 1 shows a bifurcation aneurysm in schematic representation.

In FIG. 1 a bifurcation aneurysm is illustrated with a blood supplying vessel Z, two branching vessels X and Y as well as the aneurysm A located in the bifurcation. The long arrows signify the flow of blood into the aneurysm A where it impinges on the aneurysm wall thus exerting outward pressure causing the aneurysm to enlarge (small arrows).

FIG. 2*a* shows a side view of an inventive implant 1 in expanded state. Implant 1 is provided with a fixing section 3 and a distal section 5, with the distal section 5 widening radially in comparison with the fixing section 3. During widening it forms into four loops 12, which in the interior of the aneurysm come to rest against the aneurysm wall, with additional separation elements being provided which are not shown here, said elements closing the neck of the aneurysm to such an extent that occlusion means introduced into the aneurysm are not allowed to escape.

Between the fixing section 3 and the distal section 5 there is a transition section 4 that has a small cross-section. From proximal (in the drawing on the left) to distal (in the drawing on the right), the filaments that are forming implant 1 originate from fixing section 3 and are closely brought together in transition section 4 after which they expand again to form the distal section 5. A sleeve 7 is arranged in the transition section 4, through which the filaments run and which holds the filaments together. The filaments extending through transition section 4 are to a certain extent movable towards each other but are prevented from expanding radially any further. In this way, high flexibility of implant 1 around the transition section 4 is achieved, so that the distal section 5 is capable of adapting also to irregular forms of an aneurysm A.

In the example shown in the figure, sleeve 7 is designed as a wire coil. This is made of a radiopaque material (impervious to x-rays) and for that reason enables the attending physician to visualize implant 1 during the placement process. At the proximal end of the fixing section 3, implant 1 terminates forming a coupling element 2 in the form of a coupling wire, via which implant 1 is connected to an introducer sheath, in particular a pusher wire.

Figure 2B:
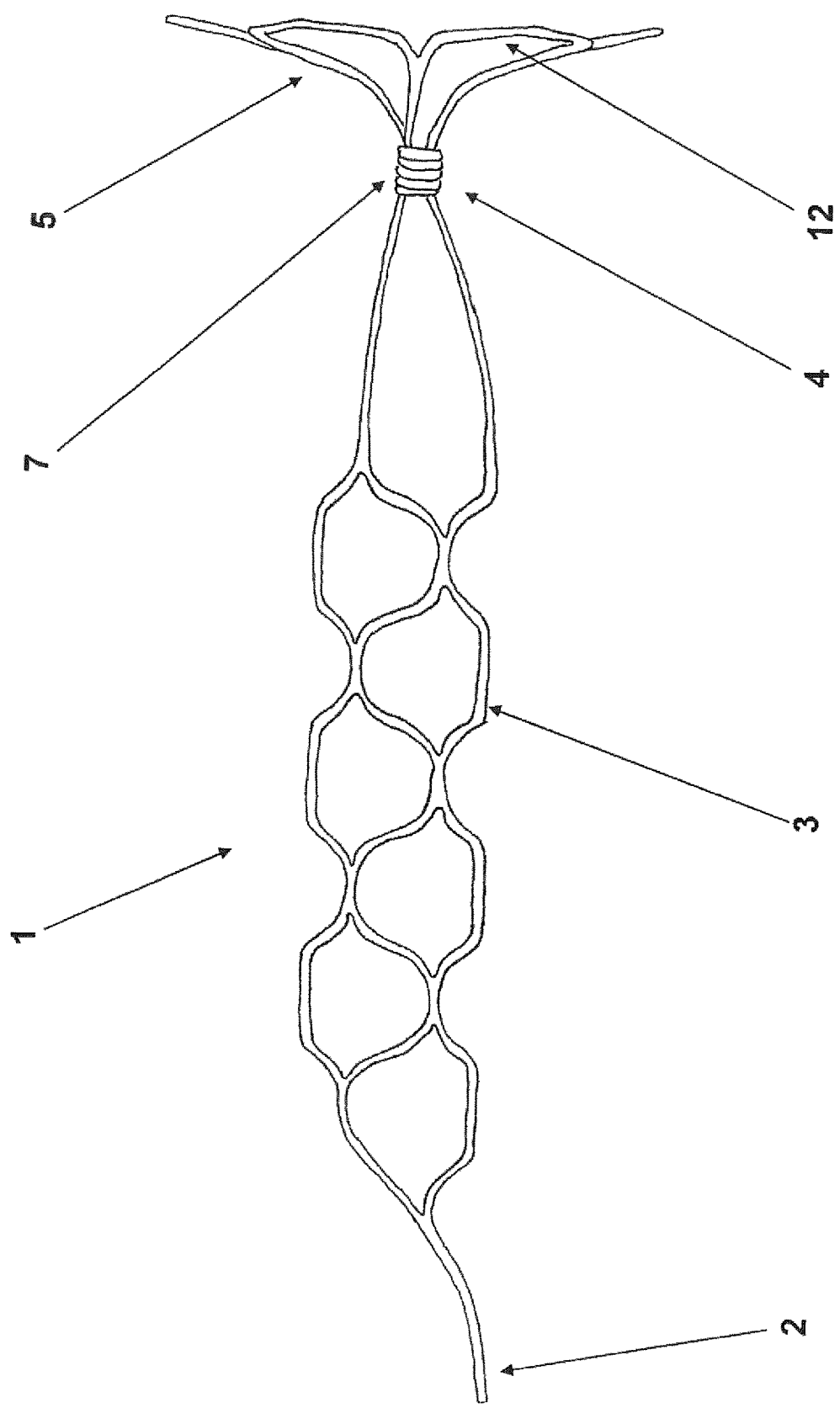
FIG. 2*b* is a side view of another inventive implant.

FIG. 2*b* shows a modified implant 1 according to the invention, whereby the representation essentially corresponds to that shown in FIG. 2*a*. However, the fixing section 3 is not of honeycomb design over its entire length, the distal area of the fixing section 3 consists of filaments largely extending straight in the direction of the transition section 4. In the fixing section 3, the number of honeycombs formed by the filaments in a sectional plane extending orthogonally to the longitudinal axis of implant 1 is three, i.e. in each sectional plane three honeycombs are arranged next to each other over the circumference of implant 1. On the other hand, the number of loops 12 arranged in the distal section 5 is higher; in this embodiment example a total of six loops 12 are formed.

Figure 2C:
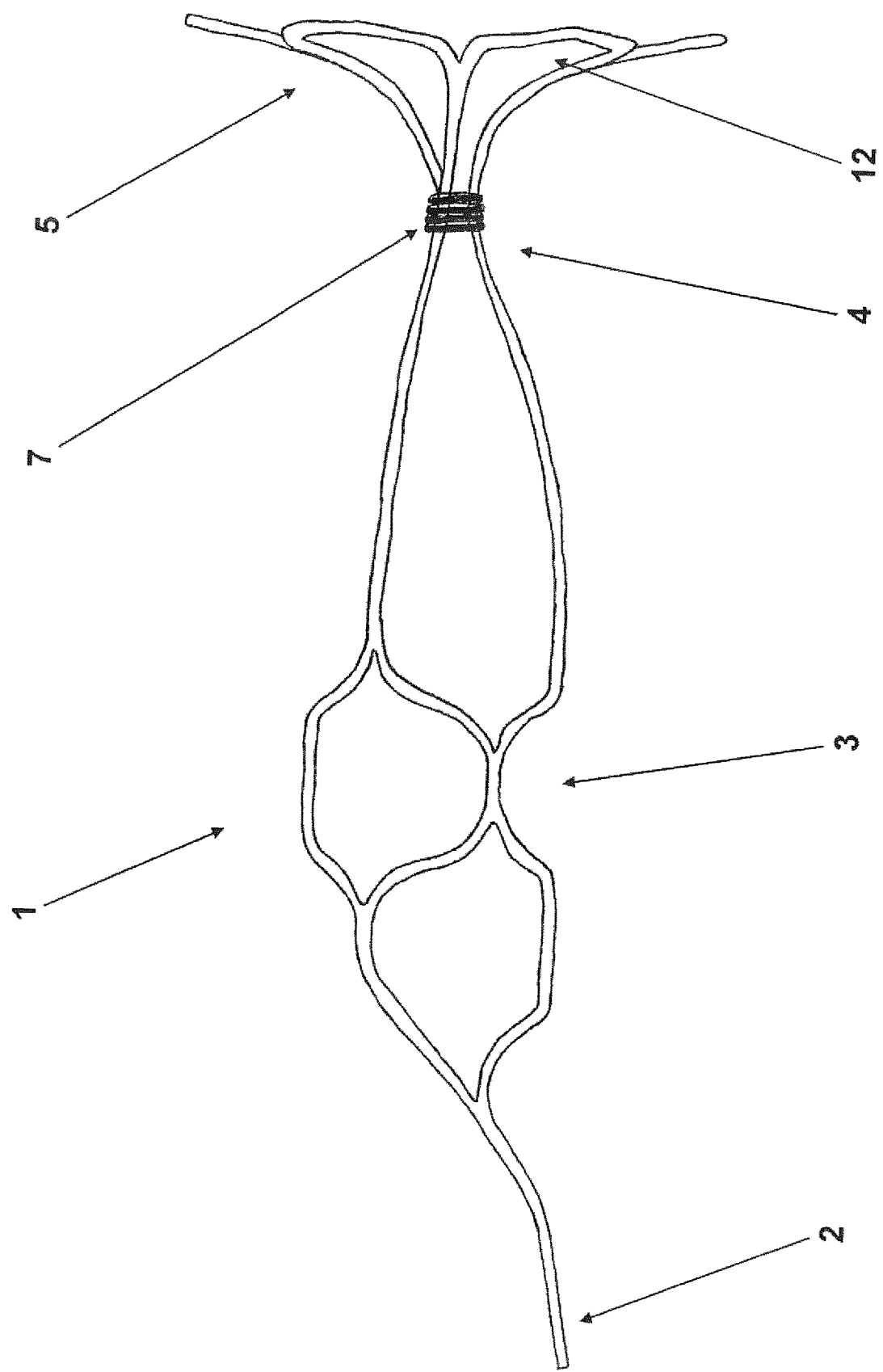
FIG. 2*c* is a side view of another inventive implant.

FIG. 2*c* shows another embodiment of implant 1 as proposed by the invention, which again essentially corresponds to the representations illustrated in FIGS. 2*a* and 2*b*. However, here the fixing section 3 is kept very short and comprises only a wreath of honeycombs. This can be particularly advantageous if the distal section 5 comprising the loops 12 is intended to be placed not inside but in front of the aneurysm. As in the embodiment example depicted in FIG. 2*b*, the number of honeycombs in fixing section 3 along a perimeter line is three and the number of loops 12 is six in total.

Figure 2D:
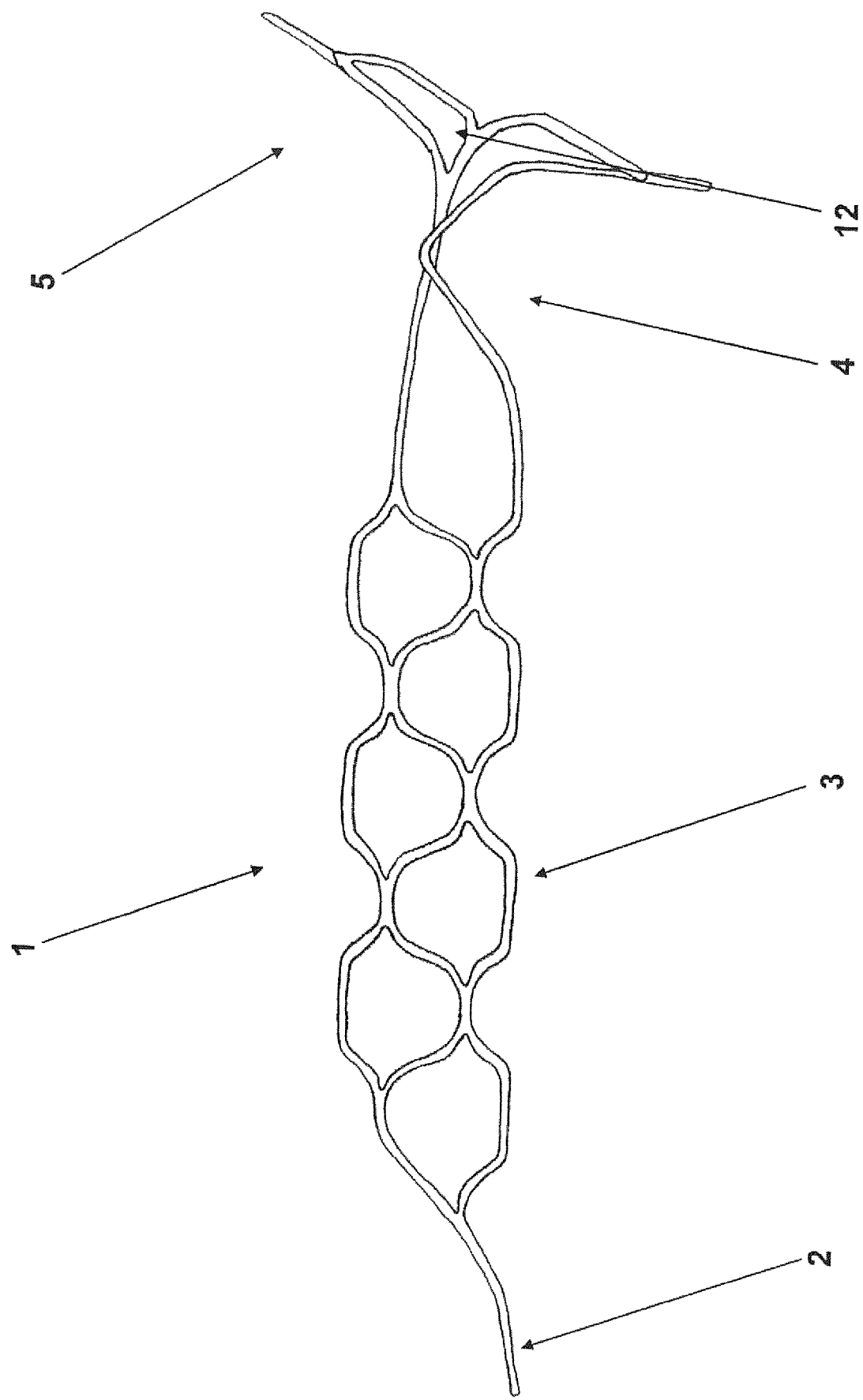
FIG. 2*d* is a side view of an implant not conforming to the invention.

In FIG. 2*d* a variant is shown which is not in accordance with the invention and differs from FIGS. 2*a* to 2*c* in that the transition section 4 has not been provided with a sleeve 7. As has been indicated in the figure, this can lead to the filaments in transition section 4 being spread outwards and no longer extend directly next to each other when the distal section 5 bends or tilts, as is frequently the case with irregularly shaped aneurysms. This effect can be even more noticeable than illustrated in the figure in which case it may possibly cause the implant 1 to be unfavorably seated in the blood vessel or even lead to an injury of the vessel wall as a result of sharp buckling or bends forming. As proposed by the invention, this effect is avoided by the provision of a sleeve 7.

Figure 3:
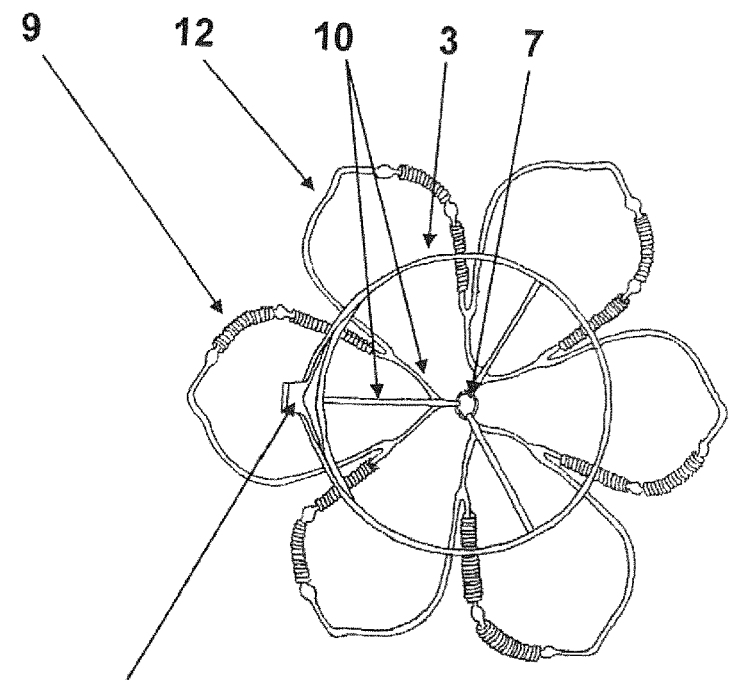
FIG. 3 shows an inventive implant viewed from the proximal side.

Seen from the proximal end, FIG. 3 shows an inventive implant 1 in the expanded state. It can be seen that the distal section 5 forms several loops 12, which stand radially outwards and provide anchorage in the aneurysm. The distal section 5 thus has a flower shape. The loops 12 are each provided on one side with a tightly wound marker coil 9 made of radiopaque material, which improves the visibility of implant 1 for the treating physician. Viewed from proximal end, the fixing section 3 can be seen here as a circle, whereby a coupling element 2 to be used for connection to the introducer sheath is provided eccentrically in the rim area of the fixing section. In the transition section, filaments 10 together pass through the sleeve 7 in the center from both the distal section 5 and the fixing section 3.

Figure 4:
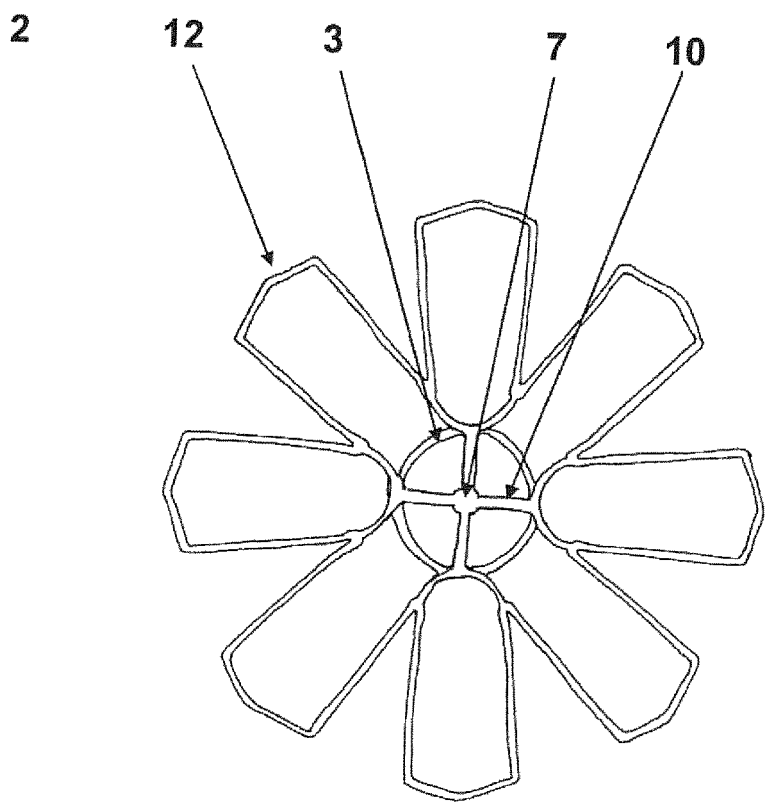
FIG. 4 shows another inventive implant viewed from the distal side.

FIG. 4 shows another inventive implant 1 in the expanded state in a view from the distal side, which differs, inter alia, from implant 1 illustrated in FIG. 3 in that a total of eight loops 12 are provided. In the background and as a cross sectional view, you can see the circular fixing section 3, from which the filaments converge centrally in the transition section through the sleeve 7. From there, filaments 10 and loops 12 extend radially outward to form the distal section 5 and obstruct the neck of the aneurysm to such an extent that occlusion means introduced into the aneurysm are prevented from exiting or the aneurysm is cut off from blood flow as effectively as possible.

Figure 5:
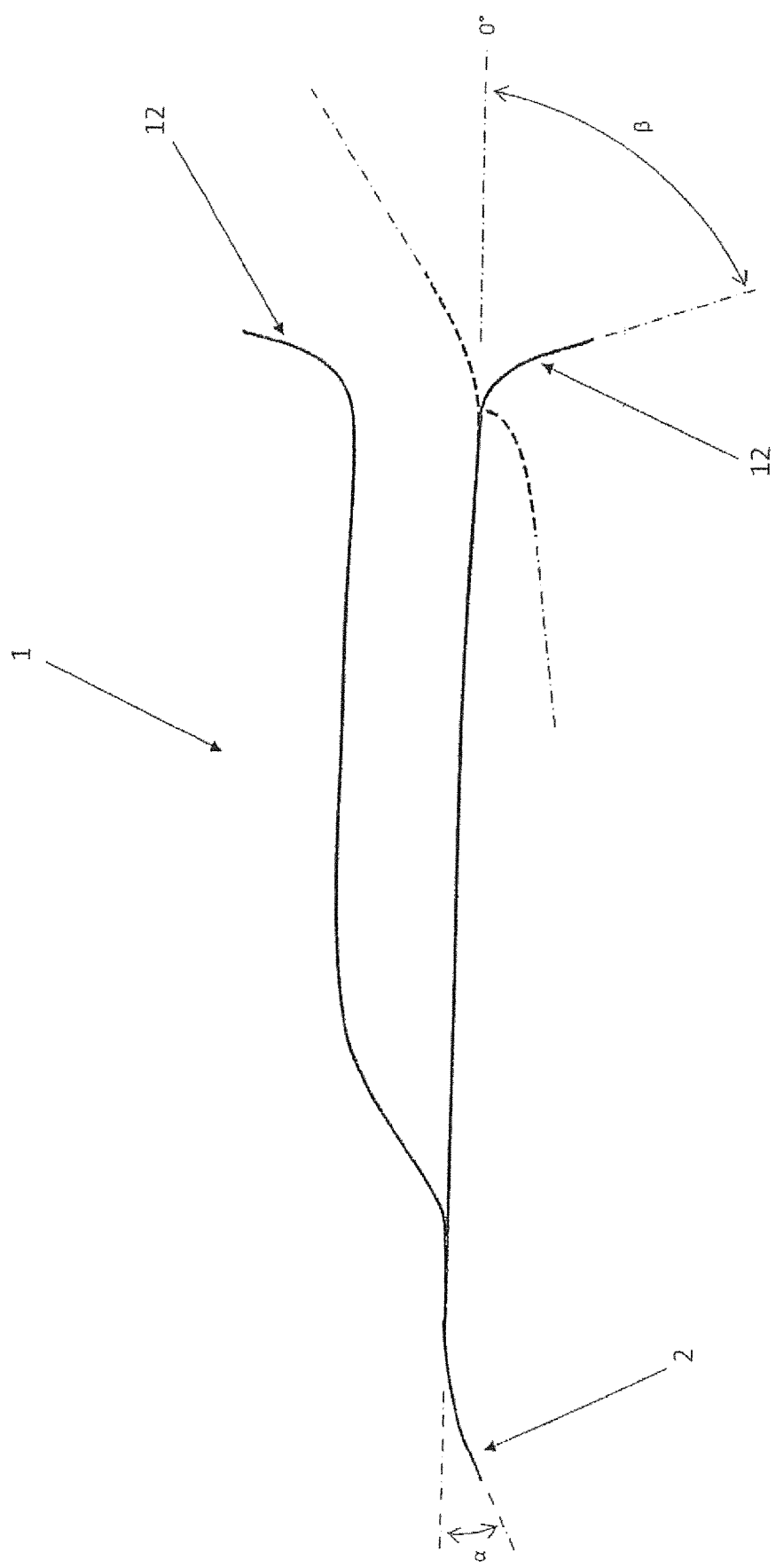
FIG. 5 is a schematic representation of a non-inventive implant in terms of the angles that the loops form in the distal section.

FIG. 5 shows schematically an implant 1, which, although not to be regarded as being in accordance with the invention due to the fact that a very narrow transition section surrounded by a sleeve is missing, illustrates the formation of different angles β of the loops 12 in relation to the longitudinal axis of implant 1 shown here only schematically. The longitudinal axis is shown as a broken line. Angle β may be very great (>90°, shown dashed) which is especially helpful with aneurysms A of greatly bulging shape wherein the bulge at least partially extends in proximal direction. In extreme cases this angle β may be almost 180°. In this way, the distal section 5 is capable of coming into close contact with the wall of the aneurysm.

In other cases (also shown dashed) it may also be of advantage to arrange for angle β to be negative in the event part of the wall of the aneurysm has an inwardly curved shape. It is to be understood as important that the angles for the individual loops 12 or even struts may differ which offers considerable advantages when treating irregularly formed aneurysms A.

It can also be seen from FIG. 5 that the proximal end 2 of the implant 1, where the implant 1 terminates forming coupling wires by means of which the implant 1 is connected to an introducer sheath, forms angle α in relation to the longitudinal axis of the implant. This angle is possibly present only in fully expanded state without external constraint exerted. Not only will the expansion of the implant 1 be improved in this way but implant contact with the wall of the blood vessel is enhanced as well and, furthermore, any undesirable projection into the blood vessel Z avoided.

Figure 6A:
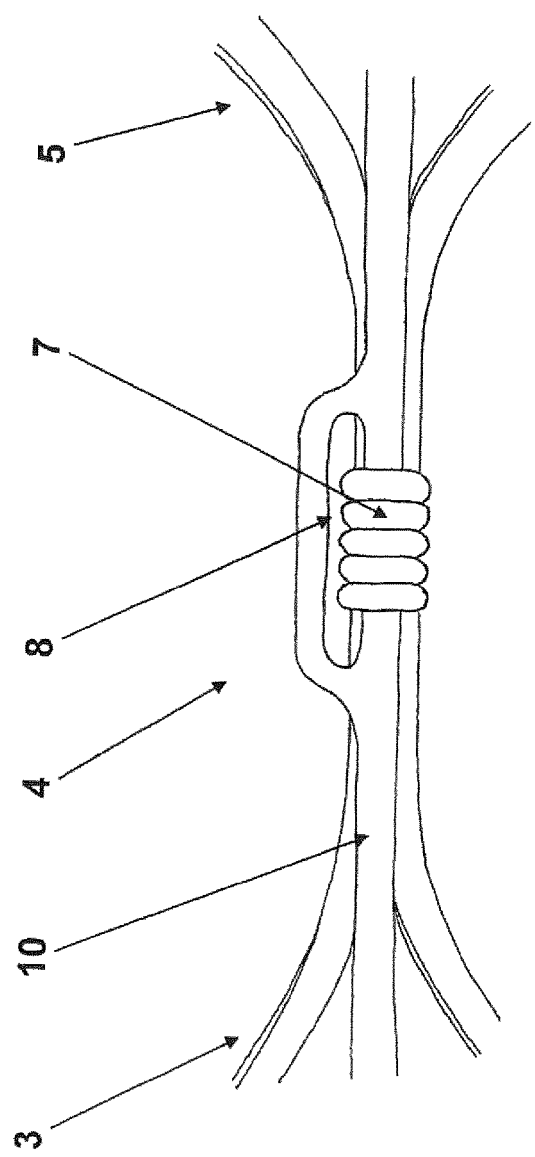
FIG. 6*a,b* shows a variant of an inventive implant with an eyelet for fixation of the sleeve.

FIG. 6a is a side view of the transition section 4 of an implant 1 in accordance with the invention, in which one of filaments 10 has an eyelet 8 located in the area of the sleeve 7. The sleeve 7 extends through the eyelet 8, so that the longitudinal slidability of the sleeve 7 is restricted. The sleeve 7 can shift up to the proximal or distal stop of the eyelet 8 at most; a further displacement, which could potentially impede the correct unfolding of implant 1, is thus safely ruled out.

Figure 6B:
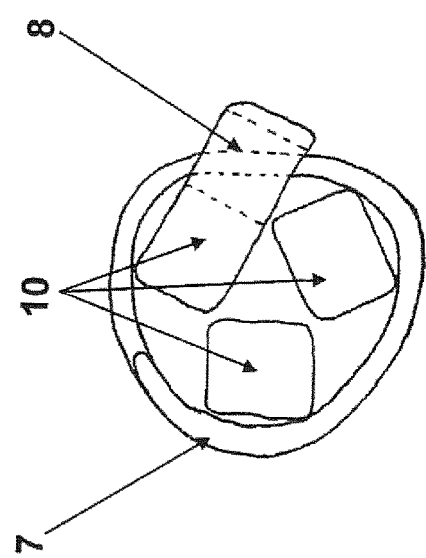

In FIG. 6b a cross-section of sleeve 7 in transition section 4 is illustrated, with three filaments 10 passing through the sleeve 7, one filament 10 of which is designed so as to be wider in the area of sleeve 7 and has an eyelet 8 through which sleeve 7 can extend.

Figure 7A:
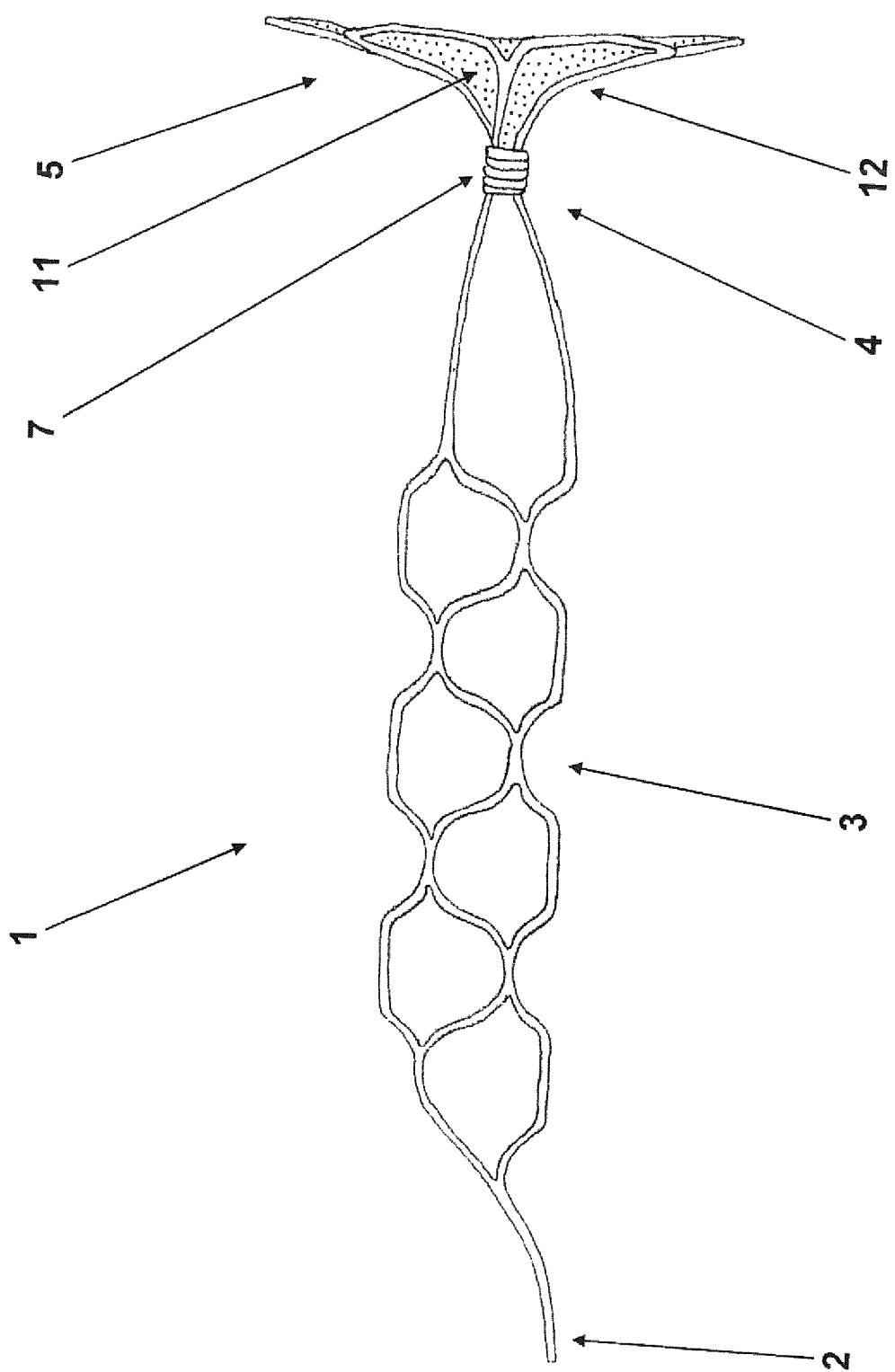
FIG. 7*a,b* is a side view and a distal view of an implant proposed by the invention with membrane covering of the loops.

FIG. 7a shows as a side view an embodiment of implant 1 as proposed by the invention, which again essentially corresponds to the representation illustrated in FIG. 2b. From this, said embodiment differs in that a membrane 11 is stretched between the filaments forming the individual loops 12 with said membranes 11 being shown dotted. Some areas between the loops 12 are also provided with a membrane 11. It is also possible to provide and arrange individual membranes 11 between the loops 12 as well as mount a single membrane 11 extending over all of the loops 12. Membrane 11 extends centrally funnel-shaped in the proximal direction and in this way enhances the separation of the aneurysm from the blood flow.

Figure 7B:
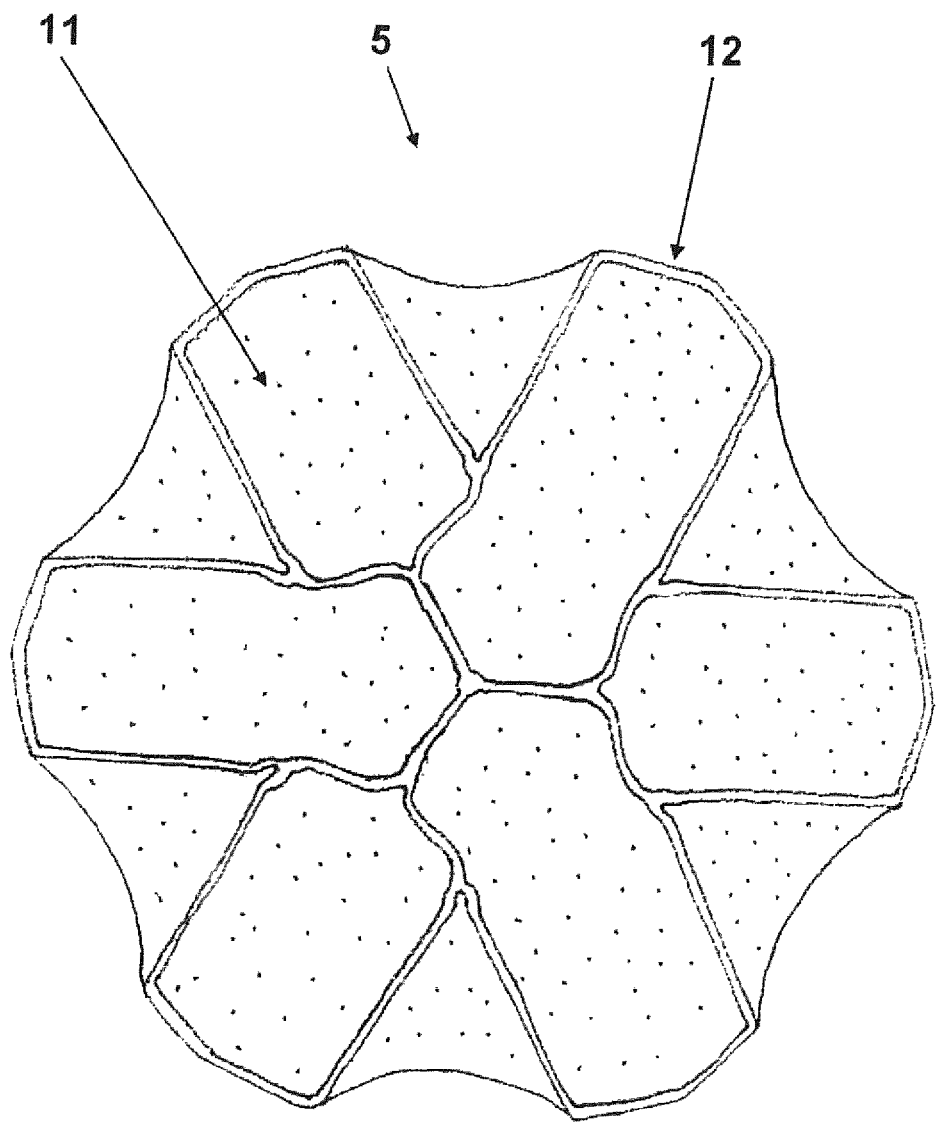

FIG. 7b is a distal view of the same embodiment from which it can be seen that the individual loops 12, but also areas between the loops 12, are provided with a membrane 11.

Figure 8:
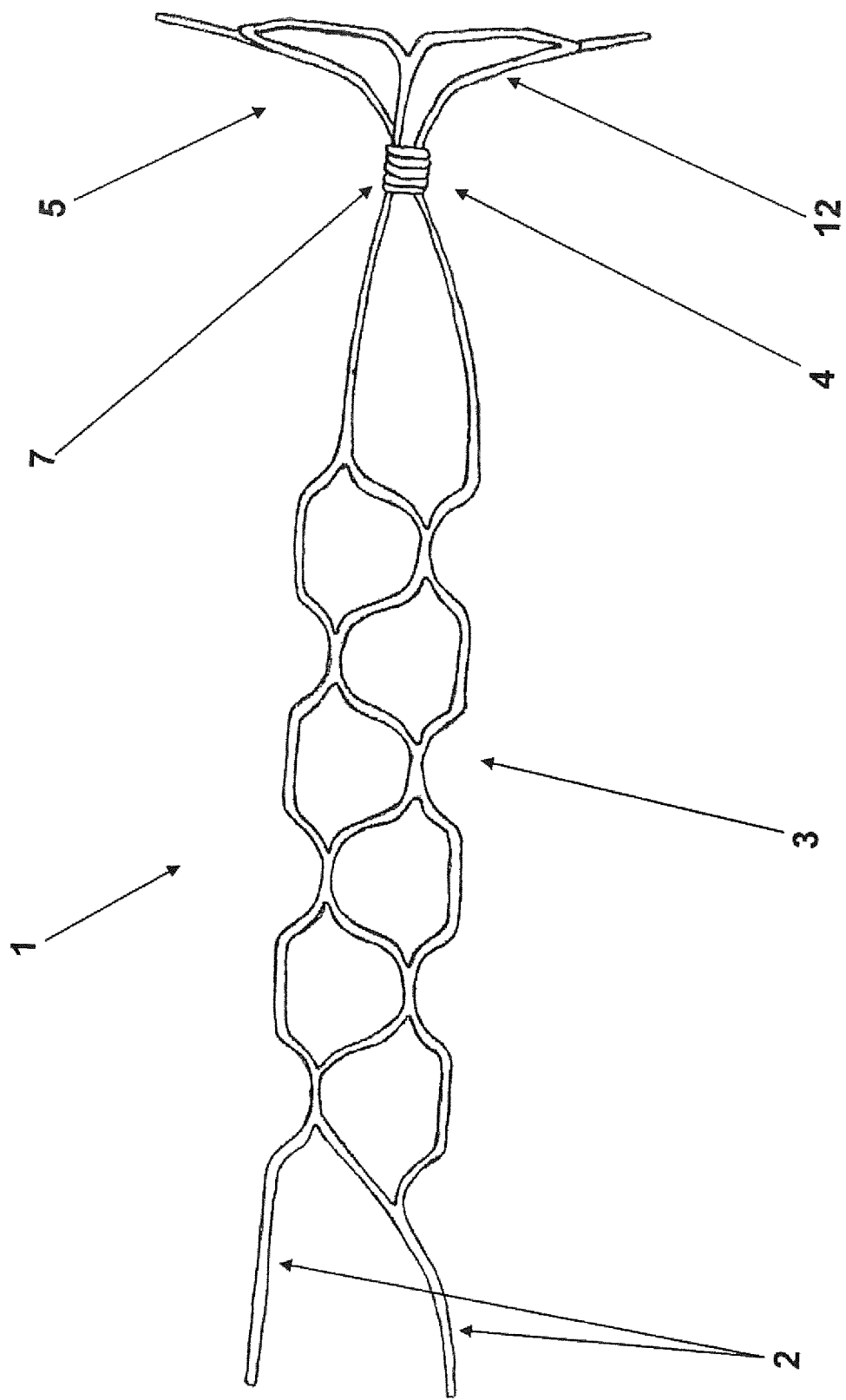
FIG. 8 shows another variant of an inventive embodiment seen from the side.

FIG. 8 shows another variant of the embodiment depicted in FIG. 2b, which is characterized in that two coupling elements 2 are provided, each of which is located in the rim area of the fixing section 3 at its proximal end. Via coupling elements 2, implant 1 is connected to an introducer sheath which has not been shown here. The provision of more than one coupling element 2 improves the retractability of the implant, especially if the fixing section 3 is very short.

The invention claimed is:

1. An implant to be used for the occlusion of aneurysms (A) in blood vessels (Z) in the region of vascular branches (X, Y), in particular bifurcation aneurysms, with
    the implant (1) having an expanded state in which it is implanted in the blood vessel (Z) and a contracted state in which it is movable through the blood vessel (Z), with the implant (1) having
    a proximal fixing section (3) by means of which the implant (1) can be secured to the wall of a blood vessel (Z),
    a distal section (5) where the implant (1) is radially widened relative to the fixing section (3) and which is intended for placement in or in front of the aneurysm (A), and having
    a transition section (4) located between the fixing section (3) and the distal section (5), wherein
    the implant (1) is composed of interconnected or intersecting filaments (10) and said filaments (10) originating from the fixing section (3) or distal section (5) meet centrally in the transition section (4), characterized in that:
    the filaments (10) in the transition section (4) at least to some extent pass through a sleeve (7); and
    at least one of the filaments (10) is provided with an eyelet (8) in the transition section (4), wherein at least a portion of the sleeve extends through the eyelet (8) and the eyelet (8) restricts the mobility of the sleeve (7) in a longitudinal direction of the implant (1).

2. An implant according to claim 1, characterized in that the sleeve (7) is formed of a wire coil with an inner cavity.

3. An implant according to claim 1, characterized in that the sleeve (7) is made at least partially of a radiopaque material.

4. An implant according to claim 1, characterized in that in the transition section (4) several filaments (10) are extending through the sleeve (7).

5. An implant according to claim 4, characterized in that the filaments (10) in the transition section (4) run parallel to each other.

6. An implant according to claim 1, characterized in that stoppers are arranged proximally and/or distally of the sleeve (7) which prevent the sleeve (7) from sliding or slipping beyond the stoppers.

7. An implant according to claim 1, characterized in that the distal section (5) comprises a plurality of struts, loops (12) or arches that at least partially are facing radially outward.

8. An implant according to claim 7, characterized in that the struts, loops (12) or arches form an angle β ranging between −45° and +175° in relation to the longitudinal axis of the implant (1), wherein a positive angle J stands for struts, loops (12) or arches pointing radially outwards and a negative angle β for struts, loops (12) or arches pointing radially inwards.

9. An implant according to claim 7, characterized in that the loops (12) or arches are provided inside with a membrane (11) or that a membrane is spanned between the struts.

10. An implant according to claim 1, characterized in that the distal section (5) is radially widened so as to from a spherical, mushroom, anchor, or ellipsoidal shape.

11. An implant according to claim 1, characterized in that one or several separation elements are arranged centrally in the distal section (5), said separation element at least partially occluding the neck of the aneurysm (A) in an implanted state.

12. An implant according to claim 11, characterized in that the one or several separation elements are formed from fibers, threads, wires or membranes (11).

13. An implant according to claim 12, characterized in that the membranes (11) extend in a proximal direction and has a conical or pyramidal form.

14. An implant according to claim 12, characterized in that each membrane (11) has one or several openings or that in each membrane (11) one or several openings can be produced by a piercing method.

* * * * *